(12) United States Patent  
Yoshida et al.

(10) Patent No.: US 8,767,513 B2  
(45) Date of Patent: Jul. 1, 2014

(54) ULTRASOUND TRANSDUCER ARRAY, METHOD OF MANUFACTURING ULTRASOUND TRANSDUCER ARRAY AND ULTRASOUND ENDOSCOPE

(71) Applicants: Olympus Medical Systems Corp., Tokyo (JP); Olympus Corporation, Tokyo (JP)

(72) Inventors: Satoshi Yoshida, Hachioji (JP); Katsuhiro Wakabayashi, Hachioji (JP); Jin Hiraoka, Sagamihara (JP); Kazuya Matsumoto, Kamiina-gun (JP); Mamoru Hasegawa, Kamiina-gun (JP); Kazuhisa Karaki, Shiojiri (JP)

(73) Assignees: Olympus Medical Systems Corp., Tokyo (JP); Olympus Corporation, Tokyo (JP)

( * ) Notice: Subject to any disclaimer, the term of this patent is extended or adjusted under 35 U.S.C. 154(b) by 0 days.

(21) Appl. No.: 13/887,525

(22) Filed: May 6, 2013

(65) Prior Publication Data

US 2013/0286786 A1    Oct. 31, 2013

Related U.S. Application Data

(63) Continuation of application No. PCT/JP2013/050911, filed on Jan. 18, 2013.

(30) Foreign Application Priority Data

Jan. 30, 2012   (JP) ................................. 2012-017220

(51) Int. Cl.  
*G01S 3/80*   (2006.01)  
*B06B 1/06*   (2006.01)  
*H04B 1/02*   (2006.01)  
*G01S 7/521*  (2006.01)  
*H04R 17/00*  (2006.01)

(52) U.S. Cl.  
CPC *G01S 7/521* (2013.01); *H04R 17/00* (2013.01)  
USPC ........................................................ 367/140

(58) Field of Classification Search  
USPC ........................................................ 367/140  
See application file for complete search history.

(56) References Cited

U.S. PATENT DOCUMENTS

| | | | |
|---|---|---|---|
| 6,465,930 B1 * | 10/2002 | Wright | 310/313 B |
| 7,512,038 B2 * | 3/2009 | Machida et al. | 367/181 |
| 7,940,603 B2 * | 5/2011 | Adachi et al. | 367/181 |
| 8,294,225 B2 * | 10/2012 | Machida et al. | 257/414 |
| 2006/0066184 A1 | 3/2006 | Sawada | |
| 2007/0249940 A1 * | 10/2007 | Kohno | 600/463 |
| 2007/0293762 A1 | 12/2007 | Sawada et al. | |

(Continued)

*Primary Examiner* — Isam Alsomiri  
*Assistant Examiner* — James Hulka  
(74) *Attorney, Agent, or Firm* — Scully, Scott, Murphy & Presser, P.C.

(57) ABSTRACT

An ultrasound transducer array according to an embodiment includes a substrate, a plurality of groove-like recesses arranged at a predetermined interval on one surface of the substrate, a cell region arranged between the recesses on the one surface side of the substrate, a flexible film configured to cover the substrate and the cell region and having fragility lower than fragility of the substrate, and a dividing groove having a width smaller than a width of the recess and reaching from the other surface of the substrate to the flexible film in the recess.

10 Claims, 14 Drawing Sheets

(56) References Cited

U.S. PATENT DOCUMENTS

| | | |
|---|---|---|
| 2007/0299345 A1 | 12/2007 | Adachi et al. |
| 2008/0042225 A1* | 2/2008 | Machida et al. ............... 257/416 |
| 2008/0084137 A1 | 4/2008 | Wakabayashi et al. |
| 2008/0089181 A1* | 4/2008 | Adachi et al. ................. 367/189 |
| 2009/0189480 A1* | 7/2009 | Machida et al. ............... 310/300 |
| 2010/0049054 A1* | 2/2010 | Sawada et al. ................. 600/466 |
| 2011/0140576 A1 | 6/2011 | Sawada et al. |
| 2011/0218443 A1* | 9/2011 | Sawada et al. ................. 600/459 |

* cited by examiner

ULTRASOUND TRANSDUCER ARRAY, METHOD OF MANUFACTURING ULTRASOUND TRANSDUCER ARRAY AND ULTRASOUND ENDOSCOPE

CROSS REFERENCE TO RELATED APPLICATION

This application is a continuation application of PCT/JP2013/050911 filed on Jan. 18, 2013 and claims benefit of Japanese Application No. 2012-017220 filed in Japan on Jan. 30, 2012, the entire contents of which are incorporated herein by this reference.

BACKGROUND OF THE INVENTION

1. Field of the Invention

The present invention relates to an ultrasound transducer array for forming an ultrasound transducer section having a curved shape provided on a distal end portion side of an ultrasound endoscope, a method of manufacturing the ultrasound transducer array, and an ultrasound endoscope.

2. Description of the Related Art

In recent years, an ultrasound diagnostic method for irradiating ultrasound on an inside of a body, imaging a state of the inside of the body from an echo signal of the ultrasound, and diagnosing the state of the inside of the body has been widely spread. Examples of medical apparatuses used in such an ultrasound diagnostic method include an ultrasound echo apparatus that can image a state of an inside of a body from a body surface and an ultrasound endoscope that includes an ultrasound transducer section, which transmits and receives ultrasound, at a distal end portion and can be inserted into a body and image a state in an inside of the body.

Among the medical apparatuses for ultrasound diagnosis, in particular, the ultrasound endoscope has been variously contrived to improve insertability into the body and reduce a diameter to ease pains of patients. Therefore, the ultrasound transducer section has been reduced in size and has been variously contrived to reduce the size.

In the ultrasound transducer section that is used in such an ultrasound endoscope and can realize a reduction in size, for example, a c-MUT (capacitive micromachined ultrasonic transducer: capacitive micromachined ultrasound probe) is sometimes used.

The c-MUT is formed by patterning a plurality of c-MUT cells on a substrate using a lithography technique. A flexible film is provided to cover the plurality of c-MUT cells on the substrate, whereby a c-MUT array, which is an ultrasound transducer array, is formed.

In ultrasound endoscopes of a radial scanning system and a convex scanning system, the ultrasound transducer section needs to be formed in a curved shape.

Therefore, in a publicly-known conventional method, a c-MUT array including transducer elements configured by a plurality of c-MUT cells is subjected to dicing using a dicing saw to form dividing grooves respectively in the c-MUT cells to form the transducer elements. Thereafter, the c-MUT array is bent to the dividing groove side to reduce width of the plurality of dividing grooves, whereby an ultrasound transducer section having a curved shape is formed.

Examples of such an ultrasound transducer section having the curved shape include an ultrasound transducer described in Japanese Patent Application Laid-Open Publication No. 2008-110060.

The ultrasound transducer described in Japanese Patent Application Laid-Open Publication No. 2008-110060 includes a flexible sheet, a rigid body portion made of a thin-film conductive material on a surface on one side of the flexible sheet, dividing portions, which are dividing grooves, for dividing the rigid body portion into a plurality of pieces to be apart from one another, and a transducer element including c-MUT cells including the rigid body portions divided by the dividing portions. After the dividing portions are respectively formed to reach the flexible sheet by dry etching from a surface side on which the c-MUT cells of the transducer element are arranged, the dividing portions are respectively extended to form, in a curved shape, the surface on which the c-MUT cells of the divided respective transducer elements are arranged.

SUMMARY OF THE INVENTION

An ultrasound transducer array according to an aspect of the present invention for attaining the object includes: a substrate; a plurality of linear groove-like recesses arranged at a predetermined interval on one surface of the substrate; a cell region arranged between the recesses on the one surface of the substrate and formed by at least one ultrasound transducer cell; a flexible film configured to cover the substrate and the cell region on the one surface side of the substrate and having fragility lower than fragility of the substrate; and a dividing groove having a width smaller than a width of the recess and reaching from the other surface of the substrate to the flexible film in the recess.

A method of manufacturing an ultrasound transducer array according to an aspect of the present invention includes: a step for arranging a cell region on one surface of a substrate; a recess forming step for forming a plurality of linear recesses, which are arranged at a predetermined interval on the one surface of the substrate, such that the cell region is located between the recesses; a filling step for filling a low fragility material having fragility lower than fragility of the substrate in the recess to fill up the recess; a flexible film forming step for covering the substrate and the cell region with a flexible film having fragility lower than the fragility of the substrate on the one surface side of the substrate; and a dividing groove forming step for forming a dividing groove reaching from the other surface of the substrate to the flexible film in the recess and having a width smaller than a width of the recess.

An ultrasound endoscope according to an aspect of the present invention is an ultrasound endoscope in which the ultrasound transducer array according to the aspect of the present invention is used.

DETAILED DESCRIPTION OF THE PREFERRED EMBODIMENTS

Embodiments of the present invention are explained in detail below with reference to the drawings.

First Embodiment

Figure 1:
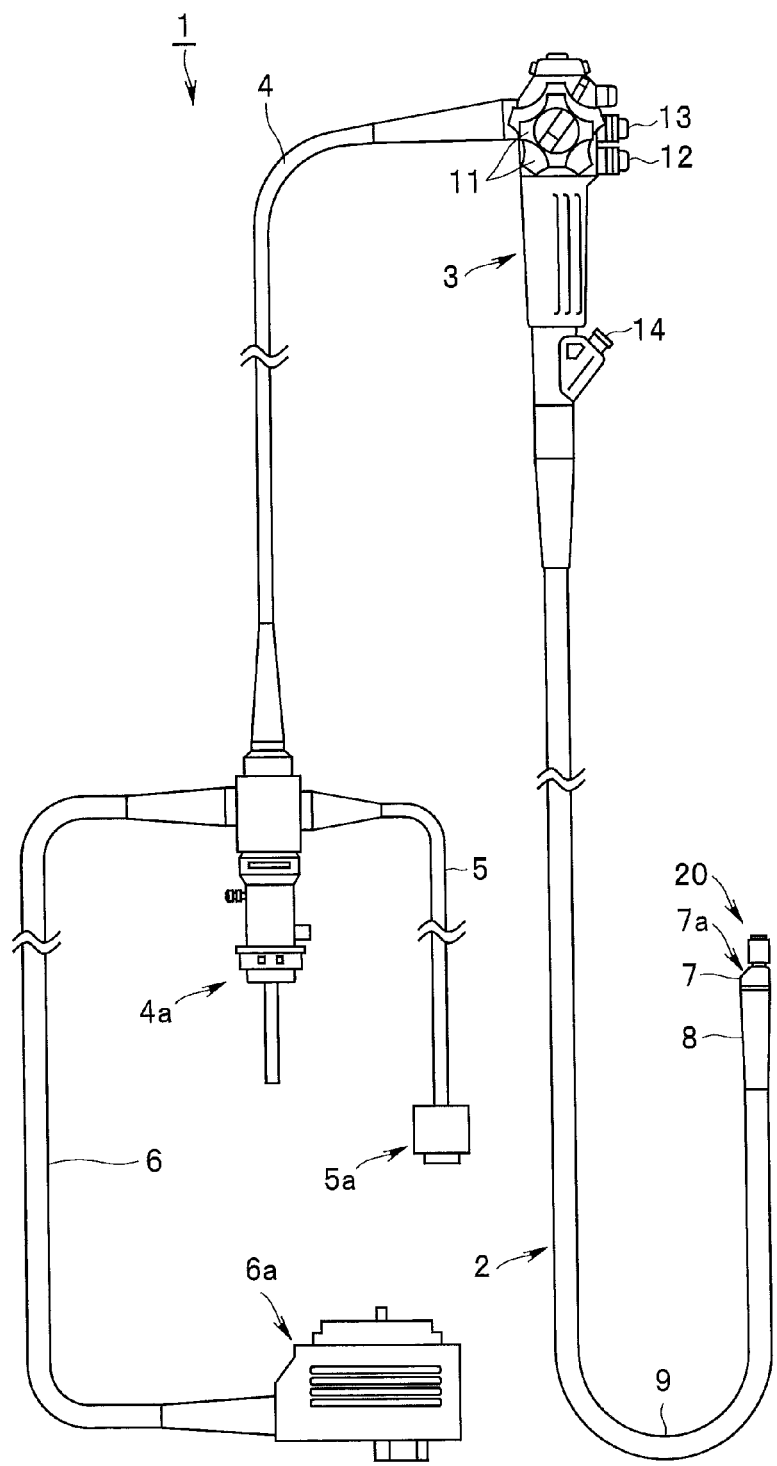
FIG. 1 is a configuration diagram for explaining a schematic configuration of an ultrasound endoscope according to a first embodiment of the present invention.
Figure 2:
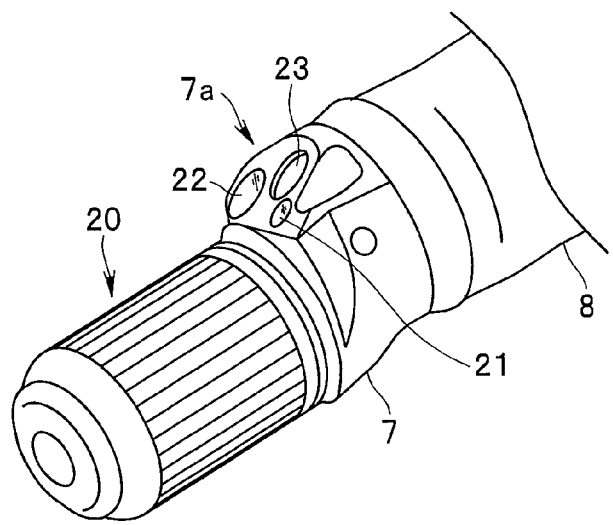
FIG. 2 is a perspective view showing a schematic configuration of a distal end portion of the ultrasound endoscope shown in FIG. 1.
Figure 3:
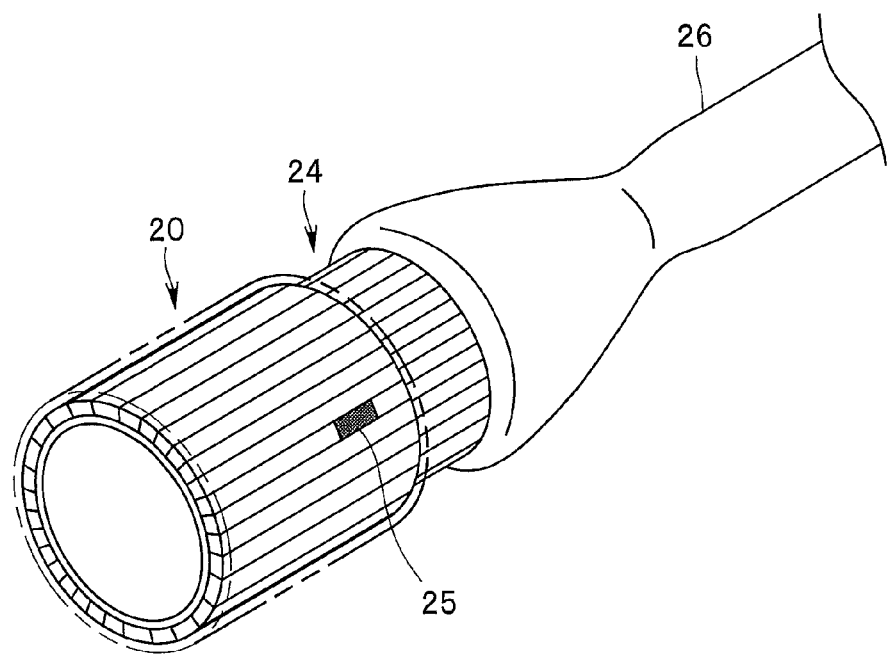
FIG. 3 is a perspective view for explaining a configuration of an ultrasound transducer section shown in FIG. 2.
Figure 4:
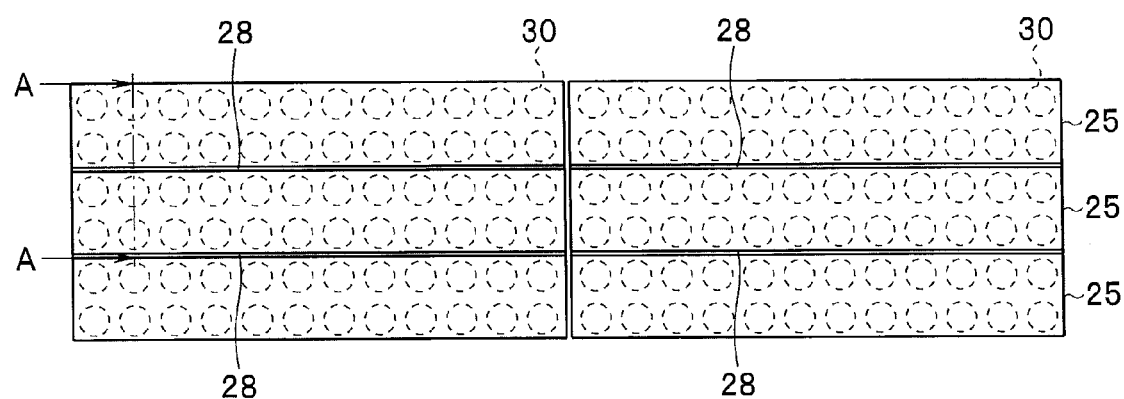
FIG. 4 is a bottom view of an ultrasound transducer array for forming the ultrasound transducer section shown in FIG. 3.

FIGS. 1 to 14 relate to a first embodiment of the present invention. FIG. 1 is a configuration diagram for explaining a schematic configuration of an ultrasound endoscope according to the first embodiment. FIG. 2 is a perspective view showing a schematic configuration of a distal end portion of the ultrasound endoscope shown in FIG. 1. FIG. 3 is a perspective view for explaining a configuration of an ultrasound transducer section shown in FIG. 2. FIG. 4 is a bottom view of a part of an ultrasound transducer array for forming the ultrasound transducer section shown in FIG. 3.

As shown in FIG. 1, an ultrasound endoscope 1 in the present embodiment is configured mainly by an elongated insertion portion 2 inserted into a body, an operation portion 3 located at a proximal end of the insertion portion 2, and a universal cord 4 extended out from a side portion of the operation portion 3.

An endoscope connector 4a connected to a not-shown light source device is provided at a proximal end portion of the universal cord 4. From the endoscope connector 4a, an electric cable 5 detachably connected to a not-shown camera control unit via an electric connector 5a and an ultrasound cable 6 detachably connected to a not-shown ultrasound observation device via an ultrasound connector 6a are extended out.

The insertion portion 2 is configured by consecutively providing, in order from a distal end side, a distal end rigid portion 7 formed of a rigid resin member, a bendable bending portion 8 located at a rear end of the distal end rigid portion 7, and a flexible tube portion 9, which is small in diameter and long and has flexibility, located at a rear end of the bending portion 8 and reaching a distal end portion of the operation portion 3. On a distal end side of the distal end rigid portion 7, an ultrasound transducer section 20 is provided, which is an ultrasound transmitting and receiving section in which a plurality of electronic-scanning ultrasound transducers for transmitting and receiving ultrasound are arrayed.

A material of the distal end rigid portion 7 is not specifically limited. However, the material preferably has chemical resistance or biocompatibility. Examples of the material include polysulfone. In the operation portion 3, an angle knob 11 for performing bending control of the bending portion 8 in a desired direction, an air/water feeding button 12 for performing air feeding and water feeding operation, a suction button 13 for performing suction operation, a treatment instrument insertion port 14 functioning as an inlet of a treatment instrument led into the body, and the like are provided.

On a distal end face 7a of the distal end rigid portion 7 in which the ultrasound transducer section 20 is provided, as shown in FIG. 2, a lens cover for lighting 21 configuring an illumination optical system, a lens cover for observation 22 configuring an observation optical system, a forceps port 23 also functioning as a suction port, and a not-shown air/water feeding nozzle are arranged.

The ultrasound transducer section 20 is an electronic radial-type transducer distal end portion in which a vibration film of a c-MUT (capacitive micromachined ultrasound probe) configured by machining a substrate using a silicon micromachining technique is formed to face outward and, as shown in FIG. 3, a plurality of transducer elements (hereinafter simply referred to as elements) 25 having a rectangular surface are arrayed in a cylindrical shape in a minimum driving unit configured by a plurality of c-MUT cells.

As the substrate, a silicon substrate, a quartz substrate, or the like can be used.

In the ultrasound transducer section 20, a cable connection substrate portion 24 including an electrode pad electrically connected to the respective elements 25 and a GND (ground) electrode pad is consecutively provided on a proximal end side. From the ultrasound transducer section 20, a coaxial cable bundle 26, respective signal lines of which are electrically connected to the cable connection substrate portion 24, is extended. The coaxial cable bundle 26 is inserted through the distal end rigid portion 7, the bending portion 8, the flexible tube portion 9, the operation portion 3, the universal cord 4, and the ultrasound cable 6 and connected to the not-shown ultrasound observation device via the ultrasound connector 6a.

Note that electrodes on application (signal) side among the respective elements 25 are respectively structured such that electric signals from the respective cables of the coaxial cable bundle 26 are separately fed to the electrodes and are configured to be electrically unconnected.

In the respective elements 25, as shown in FIG. 4, at least one or more, here, a plurality of c-MUT cells (hereinafter simply referred to as cells) 30 are arrayed at substantially equal intervals to form a cell region. Among the respective elements 25, the respective elements 25 have dividing grooves 28, which are linear cut grooves, to separate a predetermined number of groups of cells 30. Portions separated and divided to be spaced apart at a predetermined distance by the dividing grooves 28 are formed as the elements 25, which are minimum driving unit transducers.

The ultrasound transducer section 20 is formed in a curved shape as shown in FIG. 3 by the dividing grooves 28.

In the ultrasound endoscope 1 in the present embodiment, such an ultrasound transducer section 20 formed in the curved shape is configured using a c-MUT array 40, which is an ultrasound transducer array including the plurality of cells 30.

Figure 5:
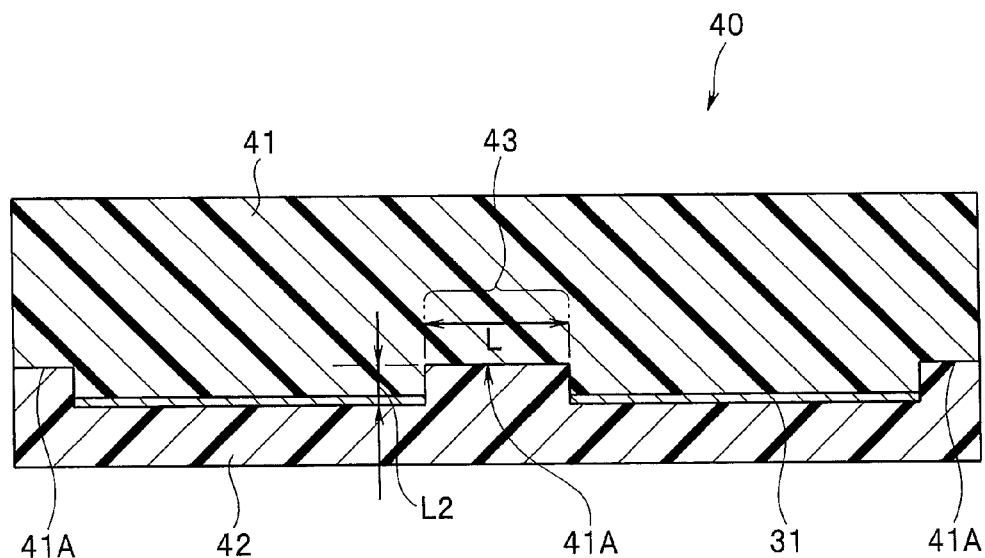
FIG. 5 is a sectional view for explaining a configuration of the ultrasound transducer array viewed from a direction extending along an A-A line in FIG. 4 and in a state before a dividing groove is formed.
Figure 6:
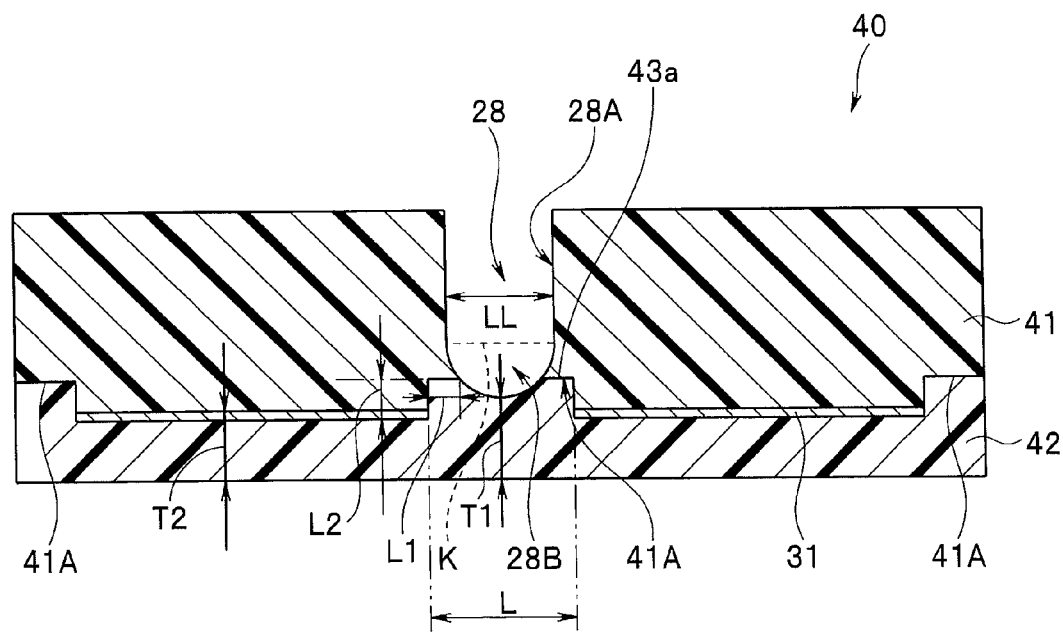
FIG. 6 is a sectional view for explaining a configuration of the ultrasound transducer array viewed from the direction extending along the line A-A in FIG. 4 and in a state after the dividing groove is formed.
Figure 7:
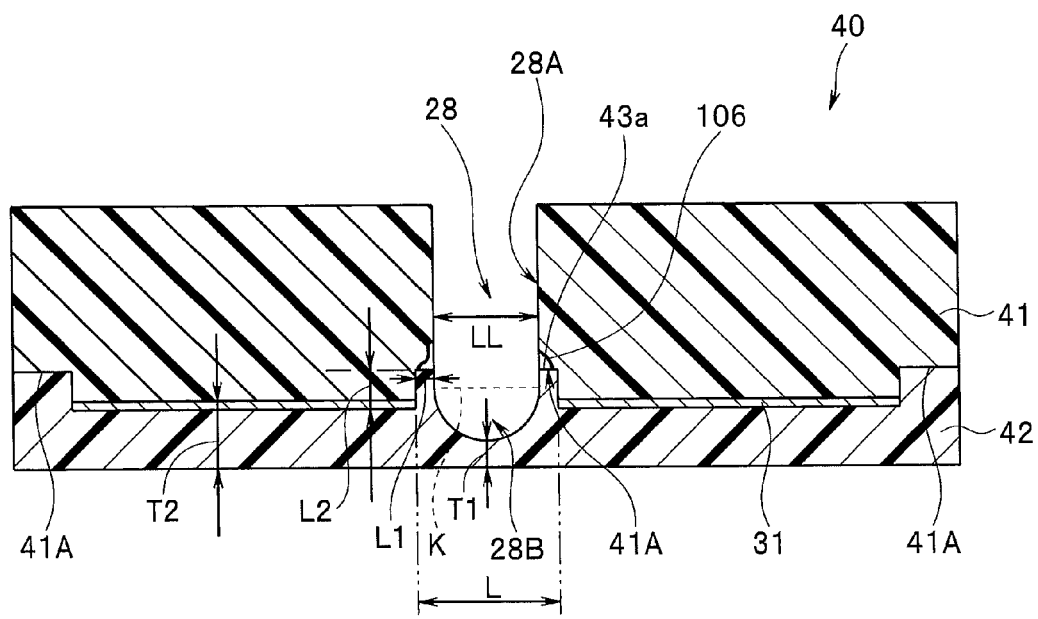
FIG. 7 is a sectional view for explaining a configuration of the ultrasound transducer array viewed from the direction extending along the line A-A in FIG. 4 and in the state after the dividing groove is formed.

Next, a specific configuration of such a c-MUT array 40 in the present embodiment is explained using FIGS. 5, 6, and 7.

Note that FIG. 5 is a sectional view for explaining a configuration of the ultrasound transducer array viewed from a direction extending along an A-A line in FIG. 4 and in a state before the dividing groove is formed. FIGS. 6 and 7 are sectional views for explaining a configuration of the ultrasound transducer array viewed from the direction extending along the line A-A in FIG. 4 and in a state after the dividing groove is formed.

As shown in FIG. 5, the c-MUT array 40 includes a substrate 41, a groove-like plurality of recesses 41A arranged at a predetermined interval on one surface of the substrate 41, cell regions 31 each including at least one cell 30 arranged among the recesses 41A on the one surface of the substrate 41, and a flexible film 42 configured to cover the substrate 41 and the cell regions 31 and having fragility lower than fragility of the substrate 41. As the substrate, for example, a silicon substrate or a quartz substrate can be used. The number of cells formed in the cell region is not specifically limited. The number can be set as appropriate according to a purpose.

The recesses 41A are linearly arranged. Concerning "linearly" referred to here, a center axis only has to be a straight line. For example, an outer circumference of the recess may be wavy or a width of a line may be changed halfway.

As a method of measuring fragility, a method indicated by JIS R 1607 can be applied.

In the c-MUT array 40 having such a configuration, the dividing groove 28 shown in FIG. 6 or 7 having a width LL smaller than a width of the recess 41A and reaching from the other surface of the silicon substrate 41 to the flexible film 42 in the recess 41A is provided by dicing using a dicing saw. The dividing groove 28 is provided to form the c-MUT array 40 in a curved shape as explained below.

A bottom surface of the recess 41A configures a street line 43 (see FIG. 5) including the width of the dividing groove 28 and serving as a cutting margin. Width L of the street line 43 is formed to be large compared with depth L2 of the recess 41A.

Note that specific numerical values of a shape of the recess 41A are described as follows: the width L of the street line 43 (width of the bottom surface of the recess 41A) is desirably, for example, 30 μm and the depth L2 of the recess 41A is desirably, for example, 10 μm. Naturally, the numerical values of the shape of the recess 41A are not limited to these numerical values and can be changed as appropriate according to width of a dicing blade 103 (see FIG. 8) used for the dicing explained below.

In particular, the width L of the street line 43 is ideally set to be the same as the thickness of the dicing blade 103 in order to manufacture the cell regions 31 in a wide area such that a larger number of cells 30 can be arranged. However, the width L only has to be set larger than the dicing blade 103 by predetermined length.

As shown in FIGS. 6 and 7, the dividing groove 28 has the width LL smaller than the width L (see FIG. 5) of the recess 41A. The dividing groove 28 includes a sidewall portion 28A, and a bottom surface portion 28B formed by forming the groove. The bottom surface portion 28B has a shape in which an interval of extended portions of the sidewall portion 28A is narrowed toward a depth direction of a groove of the dividing groove 28. In FIGS. 6 and 7, a sectional shape of the bottom surface portion 28B is a semicircular or arcuate shape. That is, the bottom surface portion 28B has a curved surface shape.

As explained in detail below, chipping 106 tends to occur in places where the dividing groove 28, the substrate 41, and the flexible film 42 gather. Therefore, as shown in FIGS. 6 and 7, the recess 41A is provided to space the places where the dividing groove 28, the substrate 41, and the flexible film 42 gather and the cell regions 31 apart from each other to thereby prevent the chipping 106 from easily reaching the cell regions 31.

Further, in FIG. 7, the dividing groove 28 is formed such that a boundary K between the sidewall portion 28A and the bottom surface portion 28B is located in the recess 41A. In portions where the substrate 41 has acute angles as indicated by reference signs 101a in FIG. 13, chipping is more easily caused. Therefore, as shown in FIG. 7, the groove is formed deep with respect to the recess. This makes it possible to prevent the acute angles 101a, which easily cause chipping, from being formed. As a result, it is possible to further suppress the chipping from reaching the cell regions 31.

Note that, in the present embodiment, when width of a bottom surface portion 43a of the recesses 41A formed by providing the dividing groove 28 and respectively arranged on both sides of the sidewall portion 28A of the dividing groove 28 is represented as L1 and depth of the recess 41A is represented as L2, the dividing groove 28 is desirably formed to satisfy a relation L1<L2.

For example, if the width of the dicing blade 103 is about 20 μm, the dividing groove 28 is formed such that the width LL of the dividing groove is about 20 μm or larger, the width L1 of the bottom surface portion 43a is about 5 μm, and the depth L2 of the recess 41A is 10 μm.

The flexible film 42 is formed of, for example, polyimide (PI) having a thickness of 10 to 20 μm or exceeding 20 μm. The silicon substrate 41 covered with the flexible film 42 is formed of, for example, silicon (Si) having a thickness of several tens to several hundreds of micrometers.

Note that, in the recess 41A, polyimide (not shown in the figure), which is a low fragility material having fragility lower than fragility of the silicon substrate 41, is arranged. In the present embodiment, as shown in FIGS. 5 and 7, the same material is used for the low fragility material and the flexible film 42.

Naturally, different materials may be provided for the low fragility material and the flexible film 42 arranged in the recess 41A.

When the same material is used for the low fragility material and the flexible film 42, after melted resin is applied to surfaces of the silicon substrate 41 and the cell regions 31 to fill up the recess 41A, the flexible film 42 is formed by hardening the melted resin.

Note that when the different materials are used for the low fragility material and the flexible film 42 that fill an inside of the recess 41A, for example, the recess 41A may be filled with polyimide and coated with paraxylene polymer (Parylene), filled with polyimide and coated with epoxy resin, or filled with polyimide and coated with silicone.

The recess 41A may be filled with polyimide and spin-coated using amorphous fluorine resin. Examples of the amorphous fluorine resin include Cytop (registered trademark). Further, an elastomer material such as polyamide or polyolefin, which is heat resistant resin, may be filled in the recess 41A.

Next, a method of manufacturing the c-MUT array 40 configured as explained above and action of the c-MUT array 40 are explained using FIGS. 5 to 14.

First, as shown in FIG. 5, an operator arranges the cell regions 31 among the recesses 41A on one surface of the silicon substrate 41.

Thereafter, according to a recess forming step, the operator forms the groove-like plurality of recesses 41A arranged at a predetermined interval on the one surface of the silicon substrate 41.

In this case, the operator forms the recess 41A by, for example, applying dry etching between the cell regions 31 of the c-MUT array 40.

Next, the operator fills a low fragility material having fragility lower than the fragility of the silicon substrate 41 in the recess 41A to fill up the recess 41A. The low fragility material in this case is as explained above. Note that, in the present embodiment, polyimide, which is a material same as a material of the flexible film 42 explained below, is used as the low fragility material.

According to a flexible film forming step, the operator covers the silicon substrate 41 and the cell regions 31 with the flexible film 42 having fragility lower than the fragility of the silicon substrate 41. In this case, the operator spin-coats and heats the polyimide on the silicon substrate 41 and the cell regions 31 to form the flexible film 42 having a thickness of about 10 to 20 μm.

In this way, the c-MUT array 40 having the configuration shown in FIG. 5 and in a state before the dividing groove 28 is formed is manufactured.

Next, according to a dividing groove forming step, the operator forms the dividing groove 28 reaching from the other surface of the silicon substrate 41 to the flexible film 42 in the recess 41A and having the width LL smaller than the width L of the recess 41A in the c-MUT array 40 shown in FIG. 5 (see FIG. 7).

As a method of forming the dividing groove 28 according to the dividing groove forming step, as explained above, the dicing performed using the dicing saw is applied.

The dicing is schematically explained and a principle of occurrence of chipping due to the dicing and an influence on a cell are explained using FIGS. 8 to 13.

Figure 8:
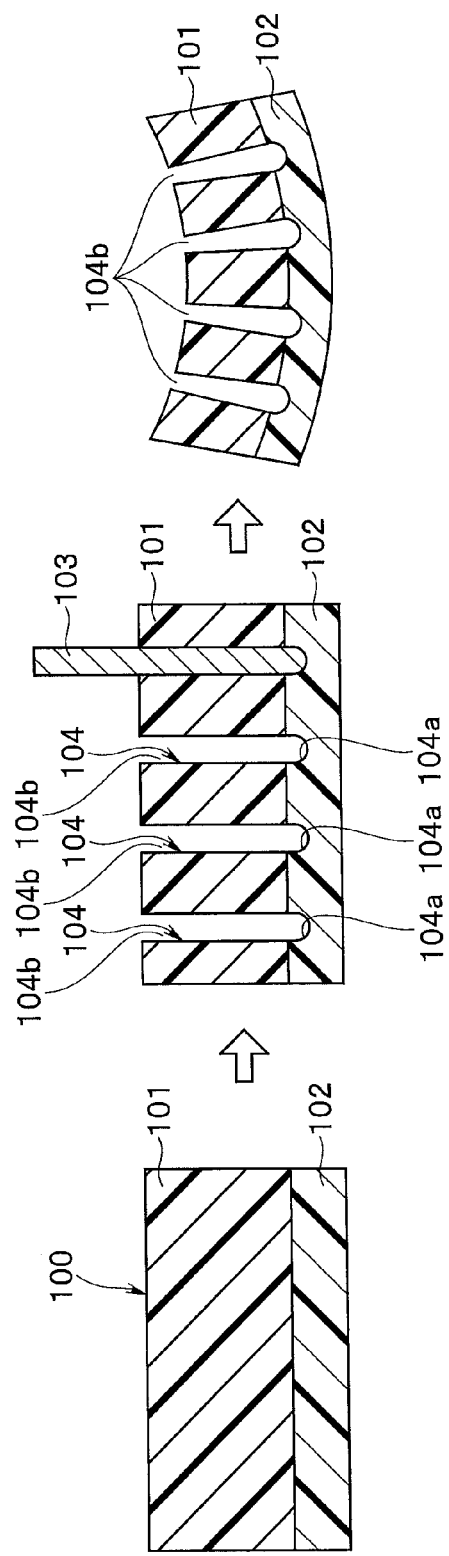
FIG. 8 is an explanatory diagram for explaining an overview of dicing for forming the dividing groove of the ultrasound transducer array.
Figure 9:
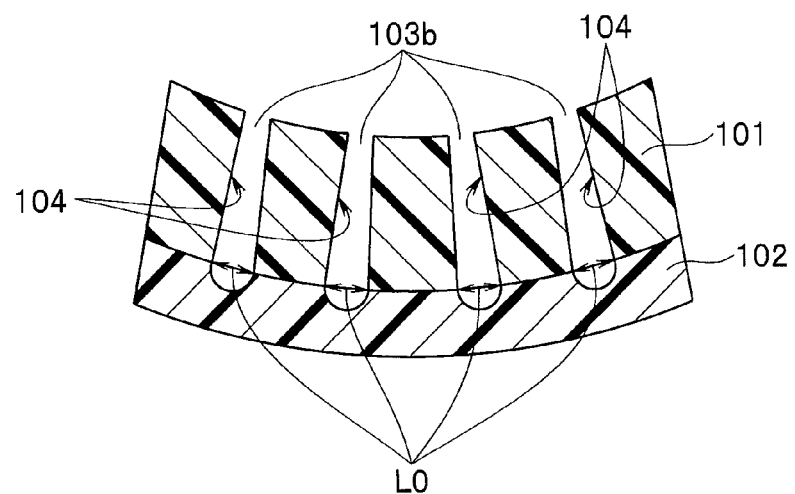
FIG. 9 is a diagram showing a state in which the ultrasound transducer array is formed in a curved shape using the formed dividing groove.
Figure 10:
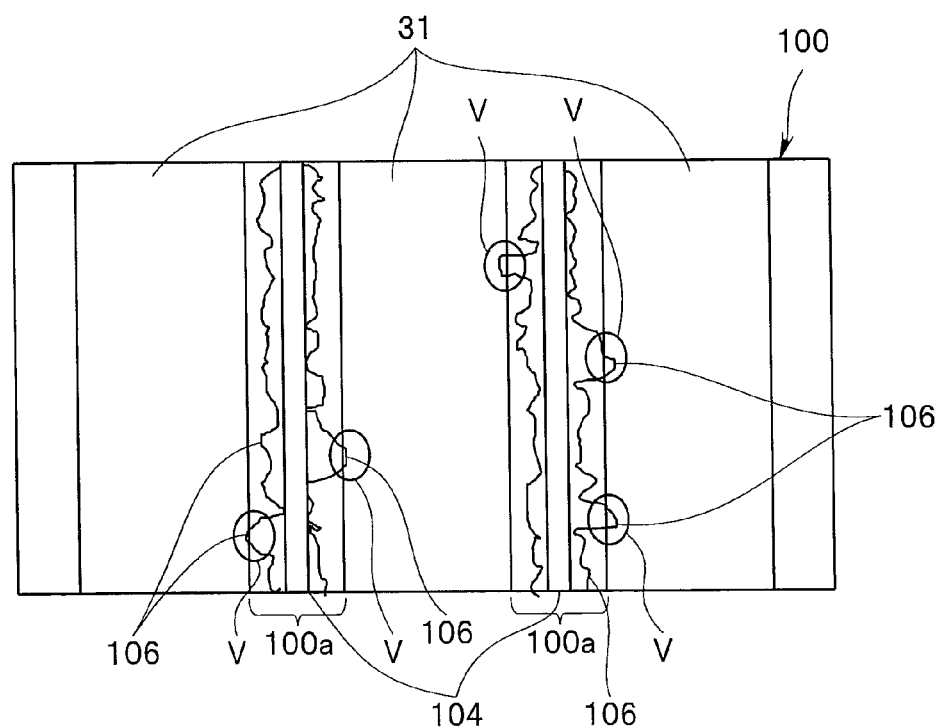
FIG. 10 is a diagram showing a state of chipping that occurs when the dividing groove is formed by the dicing.
Figure 11:
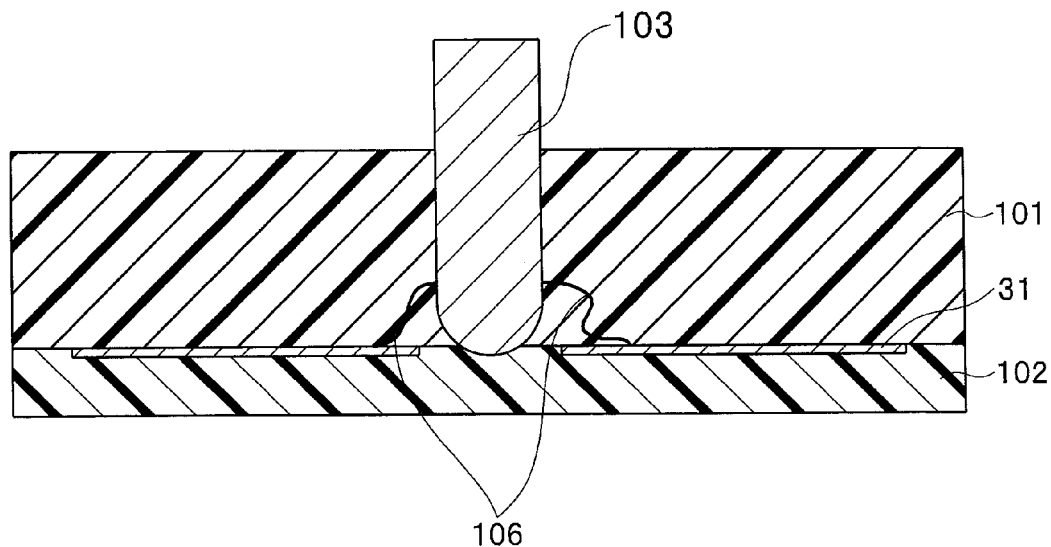
FIG. 11 is a diagram showing a state in which the chipping reaches a cell region in the ultrasound transducer array shown in FIG. 10.
Figure 12:
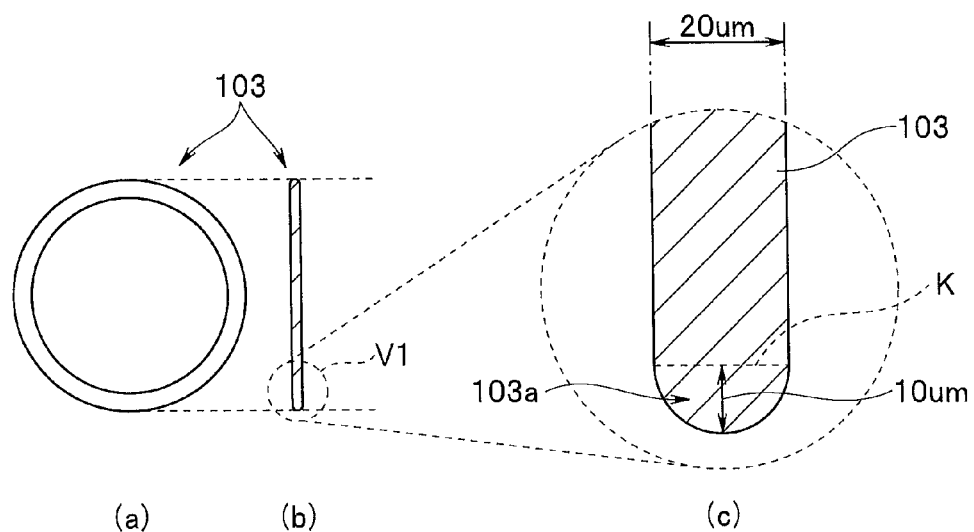
FIG. 12 is a diagram showing a shape of a dicing blade used for the dicing.
Figure 13:
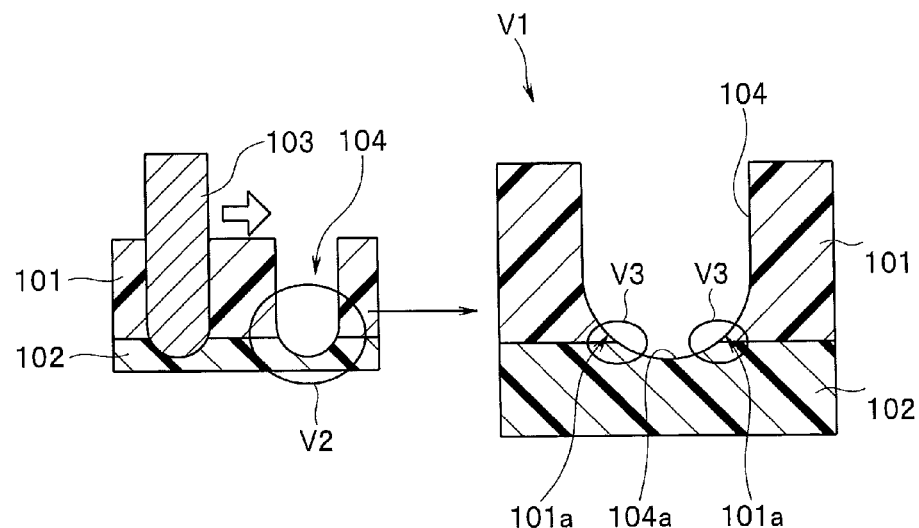
FIG. 13 is an explanatory diagram for explaining a relation between arrangement positions of a boundary portion of a flexible film and a substrate and the dividing groove and an occurrence state of the chipping.

FIG. 8 is an explanatory diagram for explaining an overview of the dicing for forming the dividing grooves of the ultrasound transducer array. FIG. 9 is a diagram showing a state in which the ultrasound transducer array is formed in a curved shape using the formed dividing grooves. FIG. 10 is a diagram showing a state of chipping that occurs when the dividing grooves are formed by the dicing. FIG. 11 is a diagram showing a state in which the chipping reaches the cell region in the ultrasound transducer array shown in FIG. 9. FIG. 12 is a diagram showing a shape of a dicing blade used in the dicing. FIG. 13 is an explanatory diagram for explaining a relation between arrangement positions of the boundary portion of the flexible film and the substrate and the dividing grooves and an occurrence state of the chipping.

As shown in FIG. 8, when the dicing is performed from a surface side of a silicon substrate 101 of a c-MUT array 100 including the silicon substrate 101, the not-shown cell region, and a flexible film 102 to form dividing grooves 104, the dividing grooves 104 are formed using the dicing blade 103 at every predetermined interval to space a not-shown predetermined number of cell groups apart from one another.

At this point, the dividing grooves 104 are formed such that bottom surface portions 104a of the dividing grooves 104 reach an inside of the flexible film 102. Openings 104b of the dividing grooves 104 are formed on a surface of the silicon substrate 101 by forming the dividing grooves 104.

As shown in FIG. 9, the c-MUT array 100 is bent in a direction of the opening 104b side to contract the openings 104b of the plurality of dividing grooves 104. Consequently, it is possible to bend the c-MUT array 100 in an arbitrary shape and in a state in which width L0 of the bottom surface portions 104a of the dividing grooves 104, i.e., a distance L0 between the elements is retained.

However, when the dividing grooves 28 are formed in the conventional c-MUT array 100 by the dicing as explained above, as shown in FIGS. 10 and 11, chipping 106 such as chips or peeling occurs in street lines 100a, which are cutting margins. The chipping 106 reaches the cell regions 31 as indicated by predetermined areas V, destroys vibrating films of c-MUT cells or reaches rear surfaces of the cell regions 31 to hinder acoustic characteristics.

The street lines 100a may be configured to be expanded to prevent the chipping 106 from reaching the cell regions 31. However, in this method, width of the cell regions 31 (see FIG. 10) that can be arranged in one c-MUT array 100 is reduced and the acoustic characteristic is deteriorated.

Therefore, it is necessary to reduce width of the street lines 100a as much as possible and improve accuracy of the dicing, for example, prevent spread of the chipping.

However, to explain a specific principle of occurrence of the chipping, as shown in FIGS. 12(a) and 12(b), the dicing blade 103 used for the dicing is formed in a disc shape. In particular, when a cross section of a distal end side portion (a portion indicated by V1 in FIG. 12(b)) in a cutting-in direction is shown in enlargement, as shown in FIG. 12(c), a cross section of a distal end portion 103a is formed in an arcuate shape having a diameter of 10 μm.

Therefore, when the width of the dicing blade 103 is set to 20 μm, an actual shape of the formed dividing groove 104 is as shown in FIG. 12(c). However, if a cut-in amount into the flexible film 102 is small, chipping tends to occur.

That is, when the cut-in amount into the flexible film 102 is small near a bottom surface portion of the dividing groove 104 shown in FIG. 13 (a portion indicated by V2 in FIG. 13), as shown in an enlarged view on a right side in the figure, since the bottom surface portion 104a of the dividing groove 104 is formed in an arcuate shape, acute angle portions 101a having an acute angle shape are formed in the silicon substrate 101 in portions where the dividing groove 104, the flexible film 102, and the silicon substrate 101 gather (portions indicated by V3 in FIG. 13). Therefore, strength of the silicon substrate 101 is reduced. Consequently, chipping tends to occur because of the acute angle portions 101a.

Therefore, in order to reduce the occurrence of such chipping, it is necessary to eliminate the formation of the acute angle portions 101a by increasing the cut-in amount to allow the arcuate shape portions of the bottom surface portion 104a of the dividing groove 104 to reach the flexible film 102. However, since the thickness of the flexible film 102 is limited, this is impossible in the conventional c-MUT array.

However, in the c-MUT array 40 in the present embodiment, since the plurality of recesses 41A are provided on the silicon substrate 41 as explained above, as shown in FIG. 14, the cut-in amount is increased to allow the arcuate shape portion of the distal end portion 103a of the dicing blade 103 to reach the inside of the recess 41A filled with the flexible film 42. Note that FIG. 14 is a diagram for explaining action of the ultrasound transducer array in the present embodiment and showing the ultrasound transducer array in a state in which chipping is reduced.

That is, the dividing groove 28 formed by the dicing blade 103 is formed such that the boundary K between the sidewall portion 28A and the bottom surface portion 28B is located in the recess 41A. In other words, the dividing groove 28 is formed such that an arcuate shape portion of the bottom surface portion 28B to be set as a radius R is located in the flexible film 42.

Figure 14:
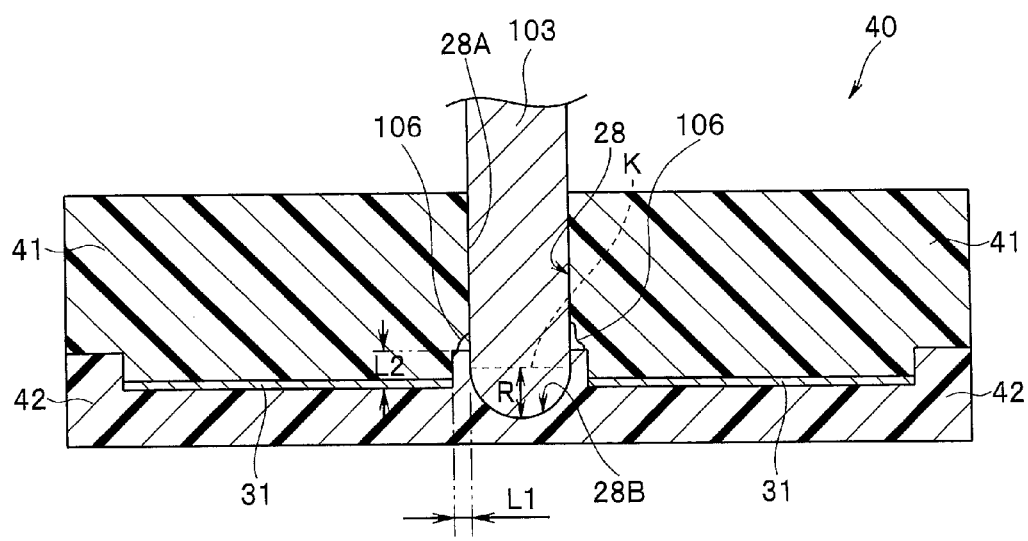
FIG. 14 is a diagram for explaining action of the ultrasound transducer array in the embodiment and showing the ultrasound transducer array in a state in which the chipping is reduced.

Therefore, in the c-MUT array 40 in the present embodiment, as shown in FIG. 14, the acute angle portions 101a explained above are not formed in the silicon substrate 41 in the portions where the dividing groove 28, the flexible film 42, and the silicon substrate 41 gather. Therefore, the strength of the silicon substrate 41 is increased. Consequently, it is possible to reduce the occurrence of the chipping 106.

Even if the chipping 106 occurs, since the recess 41A is formed with the depth L2, portions where the chipping 106 occurs are located far from the cell regions 31. The chipping 106 neither reaches the cell regions 31 nor affects the cell regions 31. Therefore, it is possible to obtain a stable acoustic effect.

The c-MUT array 40 in the present embodiment is configured to set the width L of the street line 43, which is the cutting margin, as small as possible within a range for allowing the dicing blade 103 to cut in. Therefore, it is possible to manufacture the cell regions 31 in a wide area. Consequently, since a large number of cells 30 can be arranged in the cell regions 31, it is possible to obtain a stable acoustic characteristic.

Therefore, according to the present embodiment, it is possible to realize the ultrasound transducer array 40, the method of manufacturing the ultrasound transducer array 40, and the ultrasound endoscope 1 that can reduce, with a simple configuration, without affecting the cell regions 31, which are ultrasound transducer sections, the chipping 106 that occurs when the dividing groove 28 for bending the surfaces on the cell region 31 side is formed in the silicon substrate 41.

Note that, in the present embodiment, the shape of the recess 41A is formed to be simply a square shape in the cross section orthogonal to the surface of the c-MUT array 40. However, the shape is not limited to this shape. For example, the recess 41A may be formed in a shape in a modification 1 shown in FIG. 15 or a modification 2 shown in FIG. 16.

Figure 15:
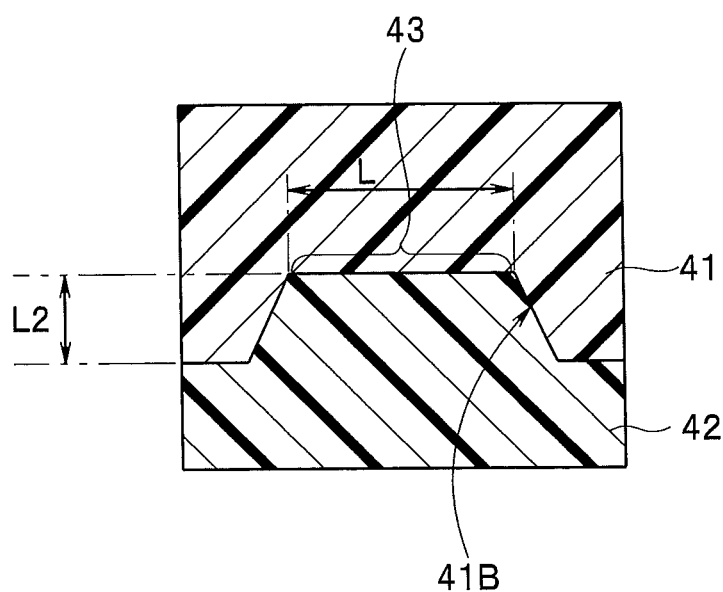
FIG. 15 is a sectional view of an ultrasound transducer array including a recess in a modification 1.
Figure 16:
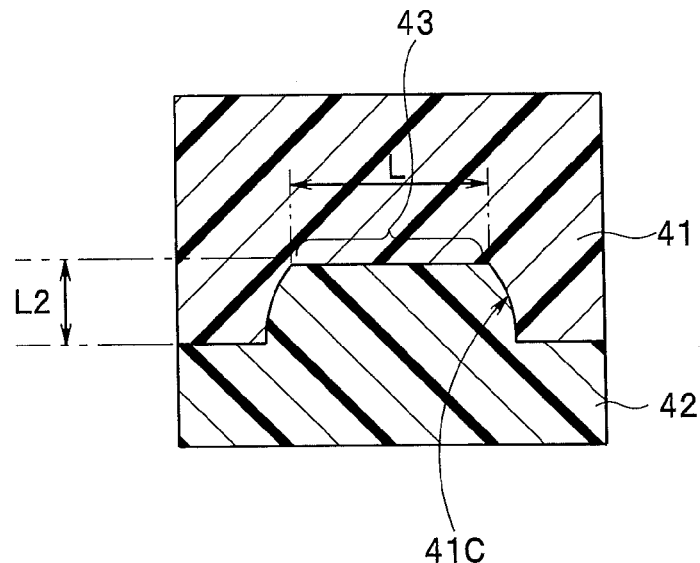
FIG. 16 is a sectional view of an ultrasound transducer array including a recess in a modification 2.
Figure 17:
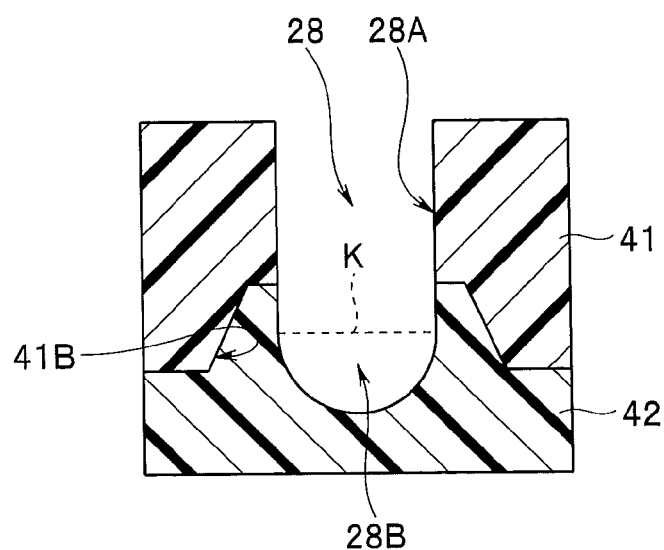
FIG. 17 is a sectional view for explaining a configuration of the ultrasound transducer array in the modification 1 in a state after a dividing groove is formed.
Figure 18:
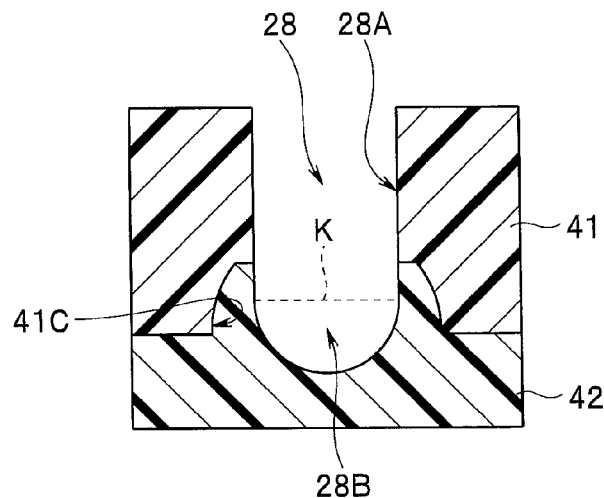
FIG. 18 is a sectional view for explaining a configuration of the ultrasound transducer array in the modification 2 in a state after a dividing groove is formed.

FIG. 15 is a sectional view of an ultrasound transducer array including a recess in a modification 1. FIG. 16 is a sectional view of an ultrasound transducer array including a recess in a modification 2. FIG. 17 is a sectional view for explaining a configuration of the ultrasound transducer array in the modification 1 in a state after a dividing groove is formed. FIG. 18 is a sectional view for explaining a configuration of the ultrasound transducer array in a modification 2 in a state after a dividing groove is formed.

In the modification 1, as shown in FIG. 15, the c-MUT array 40 includes a recess 41B, a sectional shape of which is formed in a taper shape rather than a square shape. The recess 41B includes the street line 43 having the dimension width L same as the dimension width L in the embodiment. The sectional shape is formed in the taper shape increasing in width from the street line 43, which is a bottom surface of the recess 41B, to an opening of the recess 41B.

When the dividing groove 28 is formed as in the embodiment, the c-MUT array 40 has a configuration shown in FIG. 17. That is, the dividing groove 28 is formed such that the boundary K between the sidewall portion 28A and the bottom surface portion 28B of the dividing groove 28 is located in the recess 41B.

In the modification 2, as shown in FIG. 16, the c-MUT array 40 includes a recess 41C, a sectional shape of which is not a square shape and both side surfaces of a groove of which is formed in an arcuate shape. The recess 41C includes the street line 43 having the dimension width L same as the dimension width L in the embodiment. The sectional shape is formed in the arcuate shape on both the side surfaces extending from the street line 43, which is a bottom surface of the recess 41C, to an opening of the recess 41C.

When the dividing groove 28 is formed as in the embodiment, the c-MUT array 40 has a configuration shown in FIG. 18. That is, the dividing groove 28 is formed such that the boundary K between the sidewall portion 28A and the bottom surface portion 28B of the dividing groove 28 is located in the recess 41C.

Therefore, according to the modification 1 and the modification 2, effects same as the effects in the embodiment can be obtained.

Note that, the shape of the recess 41A is not limited to the shapes in the modifications 1 and 2. The recess 41A may be formed in any shape as long as the shape can reduce the occurrence of the chipping 106.

When the thickness of a thinnest portion of the flexible film 42 in a portion where a groove is formed is represented as T1 and the thickness of the flexible film in portions where the cell regions 31 are formed is represented as T2, T1 and T2 may be the same thickness, T1 may be larger than T2 as illustrated in FIG. 6, or T1 may be smaller than T2 as illustrated in FIG. 7.

When T1 is the same as or larger than T2, there is an advantage that electric equipment safety is improved.

Second Embodiment

Figure 19:
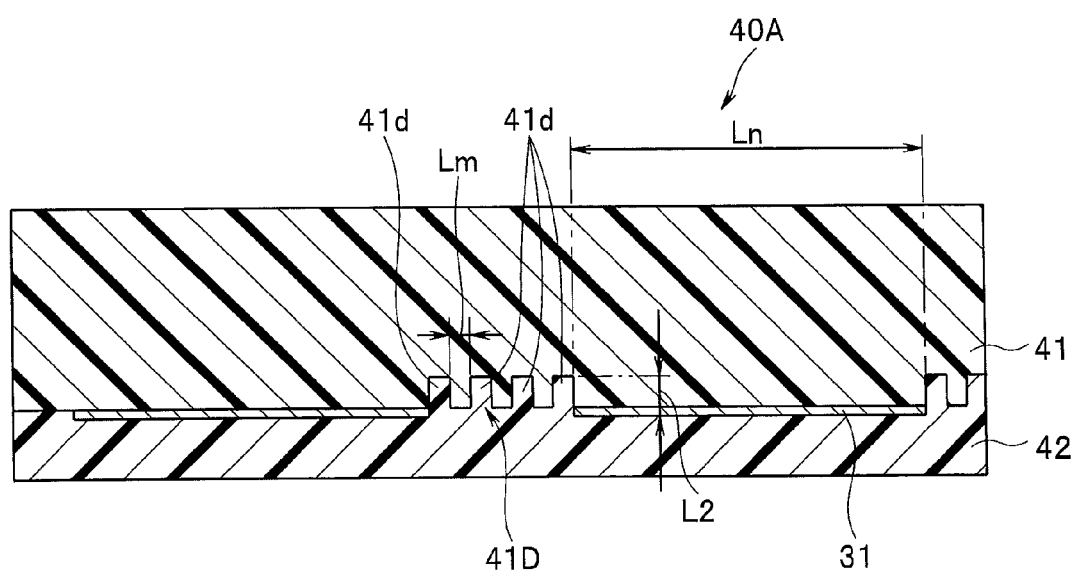
FIG. 19 is a sectional view showing an ultrasound transducer array of a second embodiment of the present invention and for explaining a configuration of the ultrasound transducer array in a state before a dividing groove is formed.

FIG. 19 is a sectional view showing an ultrasound transducer array of a second embodiment of the present invention and for explaining a configuration of the ultrasound transducer array in a state before a dividing groove is formed. Note that, in FIG. 19, components same as the components of the ultrasound transducer array in the first embodiment are denoted by the same reference numerals and signs and explanation of the components is omitted. Only differences from the first embodiment are explained.

A c-MUT array 40A in the present embodiment includes, instead of the recess 41A, a recess group 41D including at least two recesses 41d in the silicon substrate 41.

In FIG. 19, the recess group 41D includes four recesses 41d. The recesses 41d are arranged at a predetermined distance Lm, which is a first interval, from one another. A plurality of the recess groups 41D having such a configuration are arranged at a predetermined distance Ln, which is a second interval longer than the predetermined distance Lm.

Note that the recess group 41D includes the street line 43 having the same width L as in the first embodiment.

Although not shown in the figure, in the c-MUT array 40A in the present embodiment, the dividing groove 28 same as the dividing groove 28 in the first embodiment is also formed.

The other components are the same as the components in the first embodiment.

Next, a method of manufacturing a c-MUT array in the present embodiment is explained.

First, as shown in FIG. 19, an operator arranges the cell regions 31 among the recess groups 41D on one surface of the silicon substrate 41.

Thereafter, according to a recess group forming step, the operator forms the plurality of recess groups 41D each including at least two groove-like recesses 41d, which are arranged at a first interval (the predetermined distance Lm) from each other, on the one surface of the silicon substrate 41 to be arranged at a second interval (the predetermined distance Ln) larger than the first interval.

In this case, the recess groups 41D and the recesses 41d are formed by applying, for example, dry etching between the cell regions 31 of the c-MUT array 40A.

Next, according to a forming step, the operator fills up the recesses 41d using a nonconductive material and applies treatment to cover the silicon substrate 41 and the cell regions 31.

According to a flexible film forming step, the operator solidifies the nonconductive material to form the flexible film 42.

Naturally, the operator may fill a low fragility material (polyimide (PI)) having fragility lower than the fragility of the silicon substrate 41 in the recesses 41d as the nonconductive material as in the first embodiment, and spin-coat and heat the polyimide on the silicon substrate 41 and the cell regions 31 to form the flexible film 42 having a thickness of about 10 to 20 μm.

In this way, the c-MUT array 40A in the state before the dividing groove 28 is formed having the configuration shown in FIG. 19 is manufactured.

Next, according to a dividing groove forming step, the operator forms the dividing groove 28 having a width larger than the first interval (the predetermined distance Lm) from the other surface of the silicon substrate 41 and smaller than the width of the recess group 41D (the width L of the street line 43) in the c-MUT array 40A shown in FIG. 19 and reaching from the other surface of the silicon substrate 41 to the flexible film 42 in the recesses 41d. In this case, although not shown in the figure, the c-MUT 40A in which the dividing groove 28 is formed has a configuration same as the configuration in the first embodiment (see FIG. 6).

Note that, as a method of forming the dividing groove 28 according to the dividing groove forming step, as in the first embodiment, the dicing performed using the dicing saw is applied.

Therefore, the c-MUT array 40A in the present embodiment can obtain action and effects same as the action and the effects in the first embodiment even when the recess group 41D including the plurality of recesses 41d is provided.

Further, the c-MUT 40A in the second embodiment can obtain action and effects explained below. Such characteristic action and effects are explained using FIGS. 20 to 23.

Figure 20:
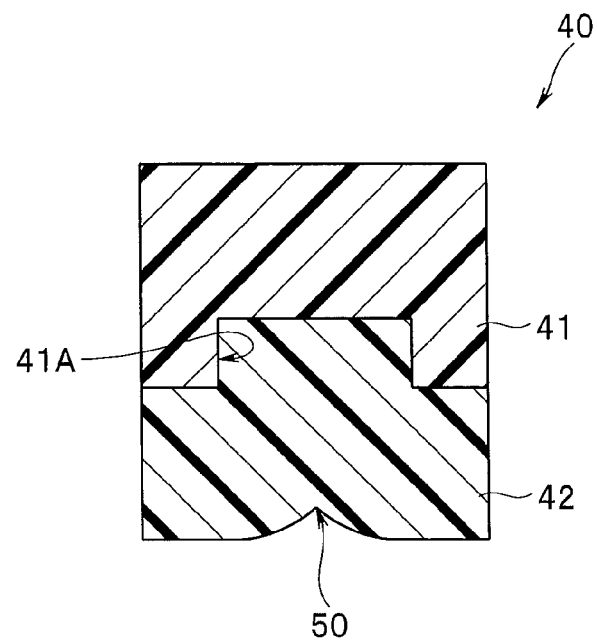
FIG. 20 is an explanatory diagram for explaining other action and effects of the ultrasound transducer array in the second embodiment before the dividing groove is formed.
Figure 21:
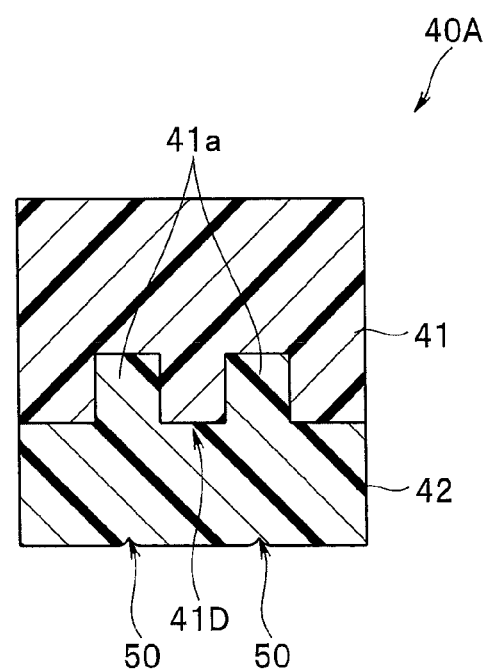
FIG. 21 is an explanatory diagram for explaining other action and effects of the ultrasound transducer array in the second embodiment before the dividing groove is formed.
Figure 22:
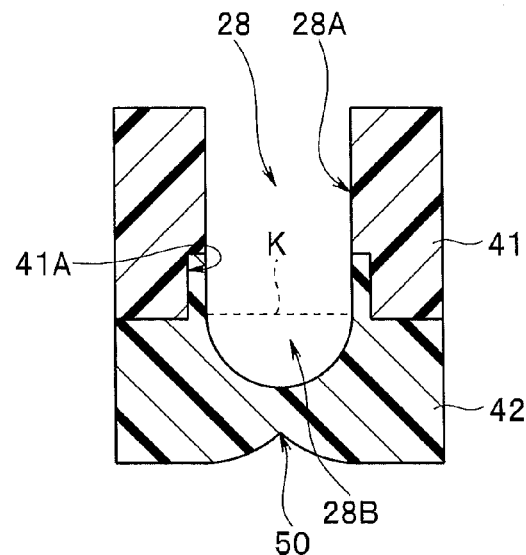
FIG. 22 is an explanatory diagram for explaining other action and effects of the ultrasound transducer array in the second embodiment after the dividing groove is formed.
Figure 23:
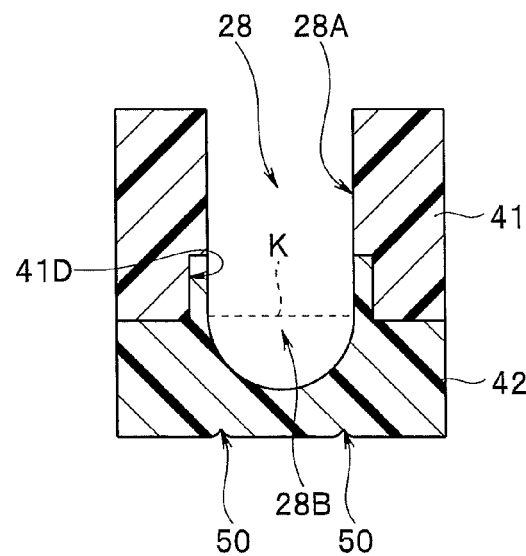
FIG. 23 is an explanatory diagram for explaining other action and effects of the ultrasound transducer array in the second embodiment after the dividing groove is formed.

Note that FIGS. 20 and 21 are explanatory diagrams for explaining the other action and effects of the ultrasound transducer array in the second embodiment before the dividing groove is formed. FIG. 20 shows a configuration in which one recess is provided. FIG. 21 shows a configuration in which two recesses are provided. FIGS. 22 and 23 are explanatory diagrams for explaining the other action and effects of the ultrasound transducer array in the second embodiment after the dividing groove is formed. FIG. 22 shows a configuration in which the dividing groove is provided in the ultrasound transducer array shown in FIG. 20. FIG. 23 shows a configuration in which the dividing groove is provided in the ultrasound transducer array shown in FIG. 21.

In the c-MUT array 40A in the second embodiment, since the plurality of recesses 41d are provided, it is possible to reduce, on a surface of the flexible film 42, a cave-in amount of a cave-in portion 50 where a part of the surface caves in.

Naturally, even when the dividing groove 28 is formed, as it is seen from FIGS. 22 and 23, it is possible to reduce the cave-in amount of the cave-in portion 50. Consequently, unevenness of a surface on a curved side of the c-MUT array 40A can be reduced. Therefore, it is possible to obtain a stable acoustic effect.

The present invention is not limited to the embodiments and the modifications explained above. Various changes, alternations, and the like are possible in a range in which the spirit of the present invention is not changed.

As explained above, according to the respective embodiments explained above, it is possible to realize an ultrasound transducer array that can prevent, with a simple configuration, chipping from easily occurring when dividing grooves for bending an ultrasound transducer array including a plurality of cells are formed on a silicon substrate.

What is claimed is:
1. An ultrasound transducer array comprising:
a substrate layer having:
a first surface;
a second surface opposed to the first surface;
a first pair of sidewalls extending from the first surface toward the second surface, wherein the first pair of sidewalls define a first recess on the first surface; and
a second pair of sidewalls extending from the second surface to meet the first pair of sidewalls, wherein the second pair of sidewalls define a second recess on the second surface;
a first cell group comprising an ultrasound transducer cell, and a second cell group comprising an ultrasound transducer cell, wherein the first cell group and the second cell group are arranged on the first surface of the substrate layer with the first recess separating the first cell group and the second cell group; and
a first low fragility material contacting the first pair of sidewalls and occupying a part of the first recess, wherein a fragility of the first low fragility material is lower than a fragility of the substrate layer,
wherein the second pair of sidewalls and a surface of the first low fragility material facing the second recess define a dividing groove extending from the second surface of the substrate layer, and wherein a minimum width of the first recess is greater than a maximum width of the dividing groove.

2. The ultrasound transducer array according to claim 1, wherein the second pair of sidewalls and the surface of the first low fragility material facing the second recess define:
a side portion of the dividing groove, the side portion extending in a depth direction of the dividing groove from the second surface of the substrate layer, wherein a width of the side portion is substantially constant; and
a bottom portion of the dividing groove, the bottom portion extending from the side portion in the depth direction, wherein a maximum width of the bottom portion is equal to or less than the width of the side portion, and wherein a boundary between the side portion and the bottom portion is located in the first recess.

3. The ultrasound transducer array according to claim 1, further comprising a second low fragility material contacting the first low fragility material,
   wherein a fragility of the second low fragility material is lower than a fragility of the substrate layer, and
   wherein the first cell group and the second cell group are interposed between the substrate layer and the second low fragility material.

4. The ultrasound transducer array according to claim 3, wherein the first low fragility material and the second low fragility material are formed of a same material.

5. The ultrasound transducer array according to claim 3,
   wherein the first low fragility material and the second low fragility material form a flexible film, and
   wherein a thickness of the flexible film adjacent to a deepest portion of the dividing groove is the same as or larger than a thickness of the flexible film adjacent to the first cell group or the second cell group.

6. An ultrasound endoscope comprising the ultrasound transducer array according to claim 1.

7. A method of manufacturing an ultrasound transducer array, the method comprising:
   a step for arranging a first cell group comprising an ultrasound transducer cell on a first surface of a substrate layer and arranging a second cell group comprising an ultrasound transducer cell on the first surface of the substrate layer, wherein the first cell group is separated from the second cell group by a first portion of the substrate layer;
   a step of removing the first portion of the substrate layer to form a first pair of sidewalls extending from the first surface of the substrate layer toward a second surface of the substrate layer opposed to the first surface, wherein the first pair of sidewalls define a first recess;
   a step of providing a first low fragility material to contact the first pair of sidewalls and to occupy the first recess, wherein a fragility of the first low fragility material is lower than a fragility of the substrate layer;
   a step of removing a second portion of the substrate layer to form a second pair of sidewalls extending from the second surface of the substrate layer to meet the first pair of sidewalls, wherein the second pair of sidewalls define a second recess; and
   a step of removing a portion of the first low fragility material, wherein, after removal of the portion of the first low fragility material, the second pair of sidewalls and a surface of the first low fragility material facing the second recess define a dividing groove extending from the second surface of the substrate layer, and wherein a minimum width of the first recess is greater than a maximum width of the dividing groove.

8. The method according to claim 7, wherein the step of removing the second portion of the substrate layer and the step of removing the portion of the first low fragility material are performed such that:
   the second pair of sidewalls and the surface of the surface of the first low fragility material facing the second recess define:
      a side portion of the dividing groove, the side portion extending in a depth direction of the dividing groove from the second surface of the substrate layer, wherein a width of the side portion is substantially constant; and
      a bottom portion of the dividing groove, the bottom portion extending from the side portion in the depth direction, wherein a maximum width of the bottom portion is equal to or less than the width of the side portion, and
   wherein a boundary between the side portion and the bottom portion is located in the first recess.

9. The method according to claim 7, wherein the step of providing the first low fragility material comprises:
   providing a melted resin to contact the first pair of sidewalls and to occupy a part of the first recess, and to interpose the first cell group and the second cell group between the substrate layer and the melted resin; and
   hardening the melted resin to form a flexible film.

10. A method of manufacturing an ultrasound transducer array, the method comprising:
   a step of arranging a first cell group comprising an ultrasound transducer cell on a first surface of a substrate layer, and arranging a second cell group comprising an ultrasound transducer cell on the first surface of the substrate layer, wherein the first cell group is separated from the second cell group by a first portion of the substrate layer, and wherein the first portion of the substrate layer has a first width;
   a step of forming a first recess and a second recess in the first portion of the substrate layer, wherein the first recess and the second recess are separated by a second width;
   a step of providing a nonconductive material to the first surface of the substrate layer to fill the first recess and the second recess, and to interpose the first cell group and the second cell group between the nonconductive material and the substrate layer;
   a step of solidifying the nonconductive material, wherein the solidified nonconductive material forms a flexible film;
   a step of forming a third recess in a second surface of the substrate layer, wherein the second surface of the substrate layer is opposed to the first surface of the substrate layer; and
   a step of removing a portion of the flexible film to communicate the third recess with the first recess and the second recess to form a dividing groove extending from the second surface of the substrate layer, wherein the dividing groove has a width that is less than the first width of the first portion of the substrate layer and greater than the second width separating the first recess and the second recess.

* * * * *